United States Patent [19]

Brodnyan et al.

[11] 4,356,229

[45] Oct. 26, 1982

[54] BONDED NONWOVEN FABRICS SUITABLE FOR DIAPER COVERSTOCK

[75] Inventors: John G. Brodnyan, Langhorne; Walter G. De Witt, III, Southampton; Robert A. Gill, Abington; Gary D. Stelling, Ambler, all of Pa.

[73] Assignee: Rohm and Haas Company, Philadelphia, Pa.

[21] Appl. No.: 198,426

[22] Filed: Oct. 20, 1980

Related U.S. Application Data

[63] Continuation of Ser. No. 966,422, Dec. 4, 1978, abandoned.

[51] Int. Cl.$^3$ .............................................. D04H 1/58
[52] U.S. Cl. .................................. 428/288; 128/156; 128/155; 128/284; 128/287; 428/297; 428/913; 524/824; 524/833
[58] Field of Search ...................... 428/288, 297, 913; 128/284, 287, 155, 156; 260/29.6 TA

[56] References Cited

U.S. PATENT DOCUMENTS

| | | | |
|---|---|---|---|
| 2,931,749 | 4/1960 | Kine | 154/101 |
| 3,020,178 | 2/1962 | Sweeney | 117/155 |
| 3,157,562 | 11/1964 | Kine | 161/170 |
| 3,554,788 | 1/1971 | Fechillas | 117/140 |
| 3,616,166 | 10/1971 | Kelley | 161/148 |
| 4,066,584 | 1/1978 | Allen | 260/17.4 |
| 4,148,987 | 4/1979 | Winey | 526/316 |

*Primary Examiner*—George F. Lesmes
*Assistant Examiner*—E. Rollins Buffalow

[57] ABSTRACT

This invention concerns a nonwoven fabric particularly adapted for use as a diaper coverstock. The fabric consists essentially of fibers and a binder wherein at least 50%, by weight, of the fibers are hydrophobic fibers. The binder comprises a water insoluble, hydrophobic, emulsion copolymer of ethylenically unsaturated monomers comprising (A) 1 to 8% by weight of a monoethylenically unsaturated carboxylic acid, or a mixture thereof, (B) 50 to 75% by weight of a $C_4$ to $C_8$ alkyl acrylate or a mixture thereof, and (C) 20 to 49% by weight of methyl methacrylate, styrene, $\alpha$-methyl styrene or a mixture thereof. The fabric has sufficient wet tensile strength for use as a diaper coverstock.

24 Claims, No Drawings

BONDED NONWOVEN FABRICS SUITABLE FOR DIAPER COVERSTOCK

This is a continuation of application Ser. No. 966,422 filed Dec. 4, 1978.

BACKGROUND OF THE INVENTION

This invention relates to bonded non-woven fibrous or filamentous products. The products preferably have a carded fiber structure, or comprise fibrous mats in which the fibers or filaments are distributed haphazardly or in random array. The invention also relates to methods for producing the bonded non-woven fibrous products or shaped articles therefrom. The bonded non-woven fibrous products are useful in the production of articles of either flat or three-dimensional shape, including diaper coverstock and the like, as will be described more particularly hereinafter.

As part of the increasing attention being given to health and environmental problems, greater attention is being paid to the components of sanitary and health care fabric products such as diapers, sanitary napkins, hospital drapes, disposable sheets and bed pads. Nonwoven fabrics for these applications are required to have an adequate tensile strength and abrasion resistance when wet by water or aqueous systems such as body fluids (urine, perspiration, etc.). Generally the binders in current use for nonwoven webs are crosslinked in order to obtain an adequate level of strength and abrasion resistance of the water-wet fabric. The crosslinking is normally based on formaldehyde, usually in the form of methylolated acrylamide although aminoplast crosslinkers are also used. Such systems are described by Kine et al in U.S. Pat. No. 3,157,562 and by Kine and Matlin in U.S. Pat. No. 2,931,749. Formaldehyde is known to be a skin irritant, there is recent evidence that it is mutagenic (Kaplan, W. D. in *Science* Vol. 108, p. 43, 1948) and concern has also been expressed that it may be found to be carcinogenic. For similar reasons, other relatively hazardous components, such as acrylamide and acrylonitrile, are also to be avoided in the manufacture of polymers for use as binders for nonwoven fabrics in the sanitary and health products area.

Non-crosslinking systems have been taught as binders for non-woven fabrics for certain specialty applications. In U.S. Pat. No. 3,554,788, Fechillas teaches a water-sensitive disposable, i.e., dispersible in water and flushable in home water closets, fabric for similar sanitary and health product uses. Fechillas' binder comprises from about 70 to 90% of a water insoluble, substantially water insensitive, film-forming, non-selfcrosslinking polymer and about 10 to 30% of a water soluble polymer. The water soluble polymers are described as water sensitive binders such as hydroxyethyl cellulose, carboxymethyl cellulose, the natural gums such as guar and preferably the alginates, such as sodium alginate, having pseudo-plastic flow properties.

In U.S. Pat. No. 3,616,166, L. E. Kelley teaches a non-woven fabric bonded by a blend of a linear polymer of ethyl acrylate having a minimum film temperature not above room temperature and a viscosity average molecular weight of about 150,000 to 300,000 and a hard polymer having a minimum filming temperature of at least about 50° C. in the ratio of 60 to 90% of the former and 40 to 10% of the latter. This material is used to make a heat sealable fabric.

BRIEF DESCRIPTION OF THE INVENTION

This invention concerns a nonwoven fabric particularly adapted for use as a diaper coverstock. The fabric consists essentially of fibers and a binder wherein at least 50%, by weight, of the fibers are hydrophobic fibers. The binder comprises a water insoluble, hydrophobic, emulsion copolymer of ethylenically unsaturated monomers comprising (A) 1 to 8% by weight of a monoethylenically unsaturated carboxylic acid, (B) 50 to 75% by weight of a $C_4$ to $C_8$ alkyl acrylate or a mixture thereof, and (C) 20 to 49% by weight of methyl methacrylate, styrene, α-methyl styrene or a mixture thereof. The fabric has sufficient wet tensile strength for use as a coverstock for diapers and like sanitary and health care products. The fabric also has a suitable level of wet abrasion resistance at body temperatures. The binder copolymer is present from 10 to 100% of the dry fiber by weight. The copolymer has a molecular weight over 100,000. The hydrophobic-fiber/binder system is readily cured even at temperatures below 110° C., particularly when the fiber content is entirely hydrophobic fibers. Two especially useful embodiments are those in which the fiber content is 100% polyester and 100% polypropylene.

DETAILED DESCRIPTION OF THE INVENTION

It has been discovered that a wet-strength nonwoven fibrous product bonded by a copolymer can be obtained by the application of an aqueous emulsion of a water insoluble copolymer, or salt thereof, of monoethylenically unsaturated monomeric units as further described hereinbelow, to a web or mat of fibers. Although bonded by a polymer which normally is not crosslinked and is preferably linear, the fibrous product or fabric has wet-strength when dried and cured, even when these steps are carried out at comparatively low temperatures, including temperatures below 110° C. The drying and curing steps produce the necessary wet-stength which is demonstrated as wash resistance and as wet tensile strength of the fabric, further described hereinbelow. Being uncrosslinked the binder and the fabric may be successfully heat sealed or sealed by application of a suitable solvent since being uncrosslinked further implies that the binder is thermoplastic and that a solvent may be found in which the copolymer is soluble without the breakage of any of the chemical bonds in the copolymer. Heat sealing the coverstock to an underlayer is a production procedure favored by some diaper producers.

Generally, it is preferred that cure temperatures above 100° C. be employed to assure the complete removal of water. A temperature of 150° C. is often convenient for drying and curing except when working with those fibers which exhibit severe dimensional changes at that temperature, such as polypropylene fibers and certain other polyolefin fibers. "Curing" is a term frequently used in the preparation of crosslinked polymers to denote the process steps which result in a crosslinking reaction in the polymer. In the instant invention "curing" is not normally accompanied by polymer crosslinking, it is, however, accompanied by development of wet strength and wet abrasion resistance of the fabric.

As a pedigogical aid in teaching the invention, the processes occurring during the curing step may be considered. These may be the wetting of the fibers by the binder and the spreading of the binder so as to interlock the fibers. This mechanistic theory is not established thus is not suggested as a full explanation for the process of wet strength development. Thus, this explanation is not considered to be a binding portion of the invention. However, the development of wet strength is quite remarkable, especially so on the hard to bond hydrophobic fibers, such as polyolefin fibers, such as polypropylene fibers, and polyester fibers, such as poly(ethylene terephthalate) fibers. Further, it may be speculated that the high bonding shown under wet conditions is due to particularly favorable set of secondary valence forces such as Van der Waals forces, between the binder and the hydrophobic fibers. With both the binder and the fiber being hydrophobic and relatively non-swelling in water, bonds found between the binder and fiber are stable to wetting by aqueous fluids.

The copolymer may be applied in free acid form (—COOH groups) or in the form of an alkali metal salt, such as of sodium, potassium or lithium (e.g. —COONa groups), an ammonium salt (—COONH$_4$) or a salt of a water-soluble amine, such as methylamine, diethylamine, triethylamine, mono-, di-, or tri-ethanolamine, morpholine, etc. Generally, it is desirable to apply the copolymer dispersion at a pH at least about 5 and preferably at a pH between 6 and 10.

The fibers are present in the form of a so-called "nonwoven" mat in which they are ordered or are haphazardly distributed. The mat may be formed by carding when the fibers are of such a character, by virtue of length and flexibility, as to be amenable to the carding operation. Carding is a preferred procedure for preparation of the mat. The fibers need not be exclusively hydrophobic and may comprise natural textile fibers such as jute, sisal, ramie, hemp, and cotton, as well as many artificial organic textile fibers or filaments including rayon, those of cellulose esters such as cellulose acetate, vinyl resin fibers such as those of polyvinyl chloride, copolymers of vinyl chloride with vinyl acetate, vinlidene chloride or acrylonitrile containing a major proportion of vinyl chloride in the polymer molecule, polyacrylonitrile and copolymers of acrylonitrile with vinyl chloride, vinyl acetate, methacrylonitrile, vinyl pyridine, or with mixtures of such comonomers and containing a major proportion, from 75% to 95%, of acrylonitrile in the copolymer molecule, polymers and copolymers of olefins such as ethylene and propylene; also condensation polymers suach as polyamides or nylon types, polyesters such as ethylene glycol terephthalate polymers and the like. The fibers used may be those of one composition or mixtures of fibers in a given web. The preferred fibers are hydrophobic, such as those of polyester especially poly(ethylene terephthalate), polyolefin, especially polypropylene, and blends comprising these fibers. The thin web or fleece obtained from a single card may be treated in accordance with the present invention, but it may be desirable to superpose a plurality of such webs to build up the mat to sufficient thickness for the end use intended. In building up such a mat, alternate layers of carded webs may be disposed with their fiber orientation directions disposed at angles such as 60° or 90°, with respect to intervening layers.

The length of the fibers is also important in producing the fabrics of the present invention. The length should usually be a minimum of about 2 cm in order to produce uniform webs in the carding operation and it is preferred that the length be between 3½ and 4 cm although ones of 5 cm and even longer are useful. Very short fibers, below 1 cm in length, are also useful particularly for wet laid webs. It is generally preferred that the fibers have a denier about 1½. It is preferred that the polyester fibers be 1½ denier. The polyolefin fibers are of approximately the same denier, with the range of 1 to 3 denier being preferred, although other deniers are also useful in some instances.

The hydrophobic fibers of this invention are fibers which exhibit very little uptake of water upon water immersion or exposure to high humidity. This property is often measured by adsorption of water by a polymer film having a composition corresponding to that of the fiber or by the moisture regain of dehydrated fibers when held in an atmosphere of fixed relative humidity. Sources of such data are Scott, J. R. and Roff, W. J. et al., *Handbook of Common Polymers*, CRC Press, (Cleveland, Ohio), 1971; Sutermeister, E. *Chemistry of Pulp and Paper Making*, John Wiley & Sons, New York, 1941, and the periodical *Textile World*, McGraw Hill Publications, Atlanta, Ga. The following table is abstracted from the 1978 Textile World Man-made Fibers Chart, herein included by reference, on page 51 et. seq. of the August 1978 Textile World.

| Fiber | Moisture Regain (%/70° F./65% R.H.) |
| --- | --- |
| polyethylene terephthalate | 0.4 |
| nylon 6 | 2.8–5.0 |
| nylon 6,6 | 4.0–4.5 |
| viscose rayon | 11–13 |
| cellulose acetate | 2.5–6.5 |
| acrylic (AN) | 1.0–2.5 |
| modacrylic | 2.5–3.0 |
| polyethylene | negligible |
| polypropylene | 0.1 |
| aramid (Kelvar$^R$, Nomex$^R$ Du Pont) | 4–7 |
| Teflon$^R$ (Du Pont) | 0 |
| Spandex (polyurethane) | ca. 1 |

Hydrophobic fibers are fibers such that the moisture regain is less than 2.5% and preferably less than 1% of the fiber weight, at 70° F. and 65% R.H.. The nonwoven, wet-strength, fabric of the instant invention comprises such hydrophobic fibers, preferably in major proportion of the fiber content and more preferably having the fibers consisting essentially of hydrophobic fibers. A most preferred embodiment is one in which the fiber content is entirely hydrophobic fibers especially 100% polyester fibers, such as poly(ethylene terephthalate), and in another embodiment 100% polyolefin fibers such as polypropylene fibers. Unless otherwise specified, the term polyester fiber, when used in the examples and other disclosure hereinbelow, refers to poly(ethylene terephthalate) fibers.

The binder of the present invention is formulated using an aqueous dispersion produced by the emulsion polymerization of ethylenically unsaturated monomers. The monomers may be selected to provide various added properties in the binder. Thus, they may provide an extremely soft and flexible binder or they may provide a relatively hard and stiffer binder which impart corresponding softness or body to the bonded fibrous product. Especially useful polymers are those which yield solid polymers which have a glass transition temperature, $T_g$, below 30° C., particularly between −30° C. and 15° C., and most desirably between −20° C. and 5° C. The $T_g$ value is found by plotting the modulus of rigidity against temperature; the $T_g$ being the temperature at which the modulus first falls appreciably below the line established in the glassy region, as the temperature rises. A convenient method for determining modulus of rigidity and transition temperature is described by I. Williamson, British Plastics, 23, 87–90, 102 (September, 1950). Preferably, because of its ease, $T_g$ is determined by calculation based on the $T_g$ of homopolymers of individual monomers as described by Fox, Bull. Am. Physics Soc. 1, 3, page 123 (1956). Tables of the $T_g$ of the homopolymers are widely available and include the one in "Polymer Handbook" Section III, part 2 by W. A. Less and R. A. Rutherford.

A polymer of the desired hardness and other properties may be obtained by copolymerizing, in suitable proportions, monomers selected from those which produce soft homopolymers and those which produce hard homopolymers. The polymerizable comonomers consist essentially of ethylenically, preferably monoethylenically, unsaturated monomers which form solid polymers in the presence of free radical catalysts. For use in copolymers curable below 110° C. to form wet-strength fabric from polyester fier, as the test fiber, the monomers which produce soft homopolymers are $C_4$ to $C_8$ alkyl acrylates such as n-butyl, iso-butyl, sec-butyl, and t-butyl, the various pentyl, hexyl, heptyl and octyl, especially 2-ethylhexyl acrylates. Of course, mixtures of these monomers may be used. For binding polyester fibers 50 to 75% by weight of these "soft" monomers is used; when the fibers are polyolefin, 55 to 70% by weight of these same monomers is preferred. Of all of the soft monomers named, the most preferred is n-butyl acrylate. For the hard monomers in the case of the copolymer for the polyester fibers, preferred is 25 to 49% by weight methyl methacrylate, styrene, α-methyl styrene or a mixture of these. When the fibers are polyolefin, the hard monomer is preferably 25 to 40% by weight styrene, α-methyl styrene or a mixture of these, styrene being preferred. The acid monomer is preferably acrylic or methacrylic acid and is present at 1 to 5% by weight of the monomers in the copolymer used with polyester fibers and 1 to 6% by weight when the fibers are polyolefin. Small amounts, desirably below 10%, of other ethylenically unsaturated monomers may be used in the copolymers with the provisos that the 100° C. curability of the fabric is met, and the other monomers are copolymerizable with the required monomers.

In preferred embodiments the copolymer characterized by forming a high wet strength fabric with polyester fibers, is a copolymer of 55 to 70% and most preferably 58 to 66% butyl acrylate and 2 to 4% of methacrylic acid or acrylic acid, preferably the latter. The copolymer is preferably made from monomers which are free of safety problems, which might arise if trace amounts were left in the emulsion, such as nitriles, amides and substituted amides particularly those of acrylic and methacrylic acids. Also to be avoided are components which give rise to formaldehyde on heating or by way of chemical reaction particularly reversible chemical reactions; such monomers include methylol acrylamide and methylol methacrylamide, methoxymethyl acrylamide and other formaldehyde or aminoplast adducts of ethylenically unsaturated compounds. Formaldehyde condensates in general are to be avoided including the low molecular weight or monomeric reaction product of formaldehyde with urea, thiourea, biuret, triazines and homologs or derivatives of these such as alcohol modified derivatives. The same preferences apply to the copolymer which forms water resistant fabric with the polyolefin fibers. It is, of course, possible to crosslink the copolymer by means of crosslinkers other than those based on formaldehyde. Such crosslinkers include multivalent metal ions, such as zinc ions, and epoxide crosslinkers, such as the bis- and poly-epoxides. However, it is preferred that the copolymer not be crosslinked.

The copolymers of this invention are characterized by producing a high wet tensile strength fabric when used to bond a hydrophobic-fiber fabric. Two most preferred fabrics are: (1) a fabric made using a carded polyester web as described in Example 2 hereinbelow, and (2) fabric made from carded polypropylene webs as described in Example 4 hereinbelow. The fabric produced by binding the polyester web with a copolymer of the instant invention has a wet tensile strength, as measured on one inch wide×6.5 inch long (2.5 cm×16.5 cm) sample, extended parallel to the long direction of the sample, is greater than 1.5 kg, preferably greater than 1.8 kg and most preferably greater than 2.0 kg. In making the polypropylene fabric the general procedure of Example 4 can be used but the webs may, inter alia, be made from a 1.8 denier by 1½ inches long fiber producing a finished fabric weighing about 17 grams/yd.$^2$ (11.2 grams fiber and 5.8 grams binder). It is generally understood that the polypropylene being a lower density fiber than the polyester gives similar performance with a slightly lighter weight fabric.

As has been stated elsewhere herein, one of the principal uses of the fabric of this invention is as diaper coverstock. Diaper coverstock is a moisture-pervious facing layer which permits body fluids initially impinged thereon to pass into the internal absorbent core of the diaper. This facing layer being in contact with the body of the wearer, must be non-irritating and have an acceptable level of abrasion resistance at a temperature in the neighborhood of body temperatures. In order to do accelerated testing a rough measure of abrasion resistance may be obtained by determining the wash durability at 60° C. However, the wash durability at 43° C., moderately above body temperatures, gives results which are believed to correlate better with diaper wear testing. To be useful in diaper coverstock, the wash durability at 43° C. is such that the fabric withstands more than 10 washes. A preferred material is one which withstands more than 15 washes, more than 20 washes is more preferred, and 25 washes most preferred. The washes are performed in a Maytag household washing machine run with 8 terrycloth bath towels for ballast and at the full load, warm water settings. Failure of the fabric is observed as the tearing of the fabric into two or more pieces or such distortion and entanglement of the fabric so that it is unuseable.

Wet tensile strength measurements can be made in the machine direction or in the cross machine direction; in the latter measurement values are obtained which are between 1/6th and 1/12th of the values obtained in the machine direction measurements. More usually the machine direction values are between 7 and 10 times larger than the cross direction values and a convenient ratio to use for most calculations or specifications is 8. Thus, a machine direction value stated elsewhere herein is meant to imply a cross machine direction value approximately 1/8th as great for the same sample.

For certain applications auxiliary agents which are conventional to use in the textile industry are added to the aqueous polymer latex. Examples are soluble and insoluble dyestuffs, optical brightners, surface active substances such as emulsifiers, wetting agents, defoaming agents and foaming agents, thickening agents such as alginates, cellulose or starch ethers or esters, stabilizers such as casein, polyvinyl alcohol or ammonium salts of polyacrylic acid, biocides, pigments, fillers, etc. A preferred wetting agent for use with fibers other than polyolefins is a nonionic surfactant having an HLB (hydrophile-lipophile balance) value between about 12 and 16, preferably between 13 and 14. The wetting agent preferred for use with polyolefin fibers is Zonyl FSN (TM DuPont) a nonionic fluorocarbon surfactant; preferably used at up to about 2% solids on fabric. It is believed that the wetting agent assists penetration of the fibrous web or mat by the binder formulation.

The emulsion copolymer is obtained by emulsion polymerization of the monomers described hereinabove. Procedures for emulsion polymerization are well known in the art, such as those described in U.S. Pat. Nos. 2,754,280 and 2,795,564, a preferred procedure being that described in Example 1 hereinbelow. The copolymer has an averge molecular weight above 100,000, preferably above 300,000, and is usually in the range between 500,000 and 2,000,000 although it may be even higher. Preferably no chain transfer agent is used in the polymerization mixture, the high molecular weight contributing to the excellent strength properties. In general, it is preferred that the monomers employed are monoethylenically unsaturated although certain monomers with higher degrees of unsaturation may be used, particularly those in which only one ethylenic group readily enters into a polymerization reaction under the preferred conditions. It is preferred that the emulsion copolymer particles be below 0.15 microns in diameter with 0.10 to 0.12 microns being best.

The binder of the present invention may be applied to the web of fibers by means well known to the art, such as by spraying, dipping, priating or the like. The concentration of the binder in the polymer emulsion that is supplied to the web is normally from about 3% to about 50% by weight and is preferably from about 5% to about 15%. It is desirable for the binder to be applied uniformly throughout the web of fibers. As noted above, auxiliary agents may be present in the polymer latex.

Although the nonwoven fabric can contain a high amount, such as up to 400% by weight, of emulsion polymer on the weight of the fibers, the usual amount is in the range from about 2% to about 50%, a preferred range being about 25% to about 40%. The products obtained are useful for many sanitary uses particularly as cover cloths for table napkins, bibs, tablecloths, sanitary napkins, disposable diapers, disposable sheets, surgical dressings and compresses. The products have a desirable degree of water resistance as indicated by their wet strength and wet abrasion resistance, but at the same time, maintain a level of water permeability so as to permit transport of aqueous body fluids through the cover stock onto the underlying absorptive materials.

The curing of the treated fibrous products is effected at a temperature above the glass transition temperature ($T_g$) of the binder polymer in order to effect proper coalescense in bonding of the fibers. Heating is helpful in driving off the water and in promoting the bonding of the fibers. It is one of the particular advantages of the binders of the instant invention that the bonding to the fibers may be effected at comparatively low temperatures such as temperatures below 110° C.; higher temperatures may be employed but are not necessary for adequate wet strength. Drying and curing is not for the purpose of crosslinking the polymer, the latex system being essentially free of crosslinking components. Thus, the binder remains thermoplastic and solvent soluble in an appropriate solvent. The cure temperature is not to be so high as to melt or to degrade the integrity of the fibers in the fabric.

In the following examples, which are illustrative of the invention, the parts and percentages are by weight and the temperatures are in degrees Celsius unless otherwise expressly noted. The following abbreviations are used:

| | |
|---|---|
| SLS | sodium lauryl sulfate |
| ME | monomer emulsion |
| APS | ammonium persulfate |
| AA | acrylic acid |
| St | styrene |
| BA | n-butyl acrylate |
| t-BHP | t-butyl hydroperoxide |
| SHS | sodium hydrosulfite |
| OPE 9.7 | octylphenoxypoly(8.7)ethoxy ethanol |
| S/S | solids on solids |
| T-300 | temperature at which the 10 seconds torsional modulus is 300 kg/cm$^2$ |
| $T_g$ | glass transition temperature |
| MAA | methacrylic acid |
| MHI | methyl hydrogen itaconate |
| HEMA | hydroxyethyl methacrylate |
| EA | ethyl acrylate |
| AN | acrylonitrile |
| MOA | an equimolar mixture of acrylamide and methylol acrylamide |
| MMA | methyl methacrylate |
| MlAM | methylolacrylamide |
| VAc | vinyl acetate |
| E | ethylene |
| Bd | butadiene |

EXAMPLE 1-Preparation of Polymer Emulsion

The preparation is a gradual addition thermal process.

| Ingredients | |
|---|---|
| Kettle Charges | Monomer Emulsion (ME) |
| 885 g. Water | 987 g. Water |
| 1.8 g. SLS (28%) | 16.1 g. SLS (28%) |
| 100 g. ME | 80 g. AA |
| 4.0 g. APS in | 650 g. St |
| | 1270 g. BA |
| 25 g. Water | 3003.1 g. |
| 915.8 g. (without ME) | |

| "Cofeed" | Promoter |
|---|---|
| 4.0 g. APS | 10 g. FeSO$_4$.7H$_2$O solution (0.1%) |
| 120 g. Water | |
| 124 g. | |
| | Chases |
| | 3 { 2.5 g. t-BHP / 20 g. Water |
| | 3 { 1.5 g. SHS / 75 g. Water |

Theoretical total solids=46.5%

PROCESS

Water and SLS are charged to a 5-liter kettle and heated to 82° C. The monomer preform, a 100 g. portion of the monomer emulsion, is added, followed by the APS in water, initiator solution. Ten minutes later, gradual addition of the monomer emulsion, to which had been added the co-feed solution, is begun at 82° C. and continued at a constant rate for 2 hours, while the temperature is held at 82°–86° C. A 15-minute hold at the temperature follows the end of the gradual addition, then the reaction mixture is cooled to 55° C. The promoter solution is added, followed by t-BHP in water. Five minutes later, the SHS solution is added. This t-BHP/SHS chase is repeated twice, at 15 minutes intervals. The batch is then cooled to room temperature and filtered through cheesecloth.

Properties

| Properties | |
|---|---|
| % solids = | 46.1 |
| % conversion = | 99.1 |
| Viscosity avg. molec. wt. = | 700,000 |
| pH = | 2.1 |
| Viscostiy = | 32 cps. (Brookfield Viscometer, spindle #1 60 rpm) |

EXAMPLE 2-Polyester Fabrics

Polymer emulsions, prepared by the general procedure of Example 1, are formulated to 6% binder solids using the appropriate quantity of water. No catalyst is used except for the conventionally crosslinked polymer controls in which case 2.5% ammonium nitrate (solids/solids) is included. All mixes contain 0.5% OPE 9.7 (s/s) as wetting agent. A typical formulation is:

| Water | 521.1 g. |
|---|---|
| 25% OPE 9.7 | 0.7 g. |
| Polymer emulsion (46% solids) | 78.9 g. |

The pH of the mix may be adjusted with ammonia as desired without significantly effecting web properties; in these examples it is between 2 and 9.

Carded polyester web (0.5 oz./yd.$^2$, 17.2 g./m.$^2$) is prepared using Dacron ® Type 54W (Merge 113505) (DuPont) fiber of 1.5 denier and 1.5 in., 3.8 cm., staple length. The webs are supported between two layers of fiberglass scrim and saturated by 6% polymer solids baths on a Birch Brothers Padder at 40 lbs., 18 kg nip roll pressure with a speed of 7.6 yds./min., 6.9 m./min. The padded webs are dried for 7 minutes at 65° C. in a forced air oven. To insure that all samples receive a similar heat treatment, all webs are cured for 1.5 minutes at 150° C. except when otherwise noted. The finished fabrics weigh 0.7 oz./yd.$^2$, 24 g./m.$^2$ and contain 30% binder.

Fabrics are tested for wet tensile strength after soaking for 30 minutes in room temperature water and blotting lightly with a towel after removal from the water bath. Specimens are cut to 1"×6.5" (2.5 cm×16.5 cm) in the machine direction and are tested on an Instron ® tester with a jaw separation of 5" (12.7 cm) and an extension rate of 2" (5.1 cm)/minute.

Hardness or softness is determined, on fabrics of a test series, by a panel of six people who rate fabrics from 1—soft to 5—stiff. The highest and lowest rating for each fabric is discarded and the remainder averaged to give the final ranking.

One measure of fabric water resistance is wet abrasion resistance or the ability of the web to withstand 10, preferably 15 and more preferably 20 wash cycles in a Maytag home launderer at the full load, warm (43° C.) water setting when washed without soap and together with eight terrycloth towels for ballast. Failure is defined as the fragmentation of the fabric into two or more pieces or, alternatively, the point at which it becomes so entangled (and thus distorted) as to be judged unusable. For experimentation purposes, it is often convenient to wash test specimens at temperatures greater than 43° C. A hot water (60° C.) wash yields a more rapid disintegration of the fabric and allows a more rapid differentiation between two or more competitive binders. This is particularly useful in the case of polyester fabrics which tend to possess greater durability than do those of polypropylene. When washed at 60° C., a polyester fabric surviving 5 wash cycles can be safely assumed to be able to survive twice as many (10) cycles at 43° C. The test is discontinued after 25 wash cycles thus a value of 25 in the tables indicates the ability to survive an unknown number of cycles greater than 25. In these examples wash temperatures are 60° C. unless otherwise specified.

A test series is a group of fabrics prepared together and tested together. One member of each test series, except series F, is made using a prior art crosslinking binder, binder C1, as a control. Ratings in the hand test are relative to the control, which is not assigned the same value in different series. Thus hand test values for different series can be intercompared only via the controls, with a consequent loss of precision. Since there maybe a small series to series variation in the carded polyester web it is also preferable to use the controls as relative standards for wet strength and wet abrasion resistance.

Table I contains a description of the binder copolymers and the properties of the fabrics produced. The copolymer latex for binder E22 is so low in shear stability as to be impracticle for the instant use.

TABLE I

Properties of Polyester Nonwoven Fabrics (23.7g./m.$^2$ with 30% binder)

| Binder | Composition | Tg °C. | Water Wet Abrasion Resistance (Washes Survived) | Water Wet Tensile Strength (kg.) | Hand Panel Test 1.0 = Softest |
|---|---|---|---|---|---|
| Test Series A | | | | | |
| E2 | 60 BA/40 St | −10 | 2 | 1.5 | 3.2 |
| E4 | 60 BA/38 St/2 AA | −10 | 19 | 2.1 | 2.5 |
| E5 | 60 BA/38 St/2 MAA | −9 | 19 | 1.9 | 3.4 |
| C1 | 65 EA/25.5 BA/ 4.5 AN/3.5 MlAM/ 1.5 IA | | 23 | 1.9 | 5.0 |

TABLE I-continued

Properties of Polyester Nonwoven Fabrics (23.7g./m.$^2$ with 30% binder)

| Binder | Composition | Tg °C. | Water Wet Abrasion Resistance (Washes Survived) | Water Wet Tensile Strength (kg.) | Hand Panel Test 1.0 = Softest |
|---|---|---|---|---|---|
| Test Series B | | | | | |
| E1 | 58.5 BA/37.5 St/4 AA | −8 | 24 | 1.7 | 3.8 |
| E7 | 61 BA/35 St/4 AA | −11 | 24 | 1.8 | 3.3 |
| E8$^2$ | 63.5 BA/32.5 St/4 AA | −15 | 23 | 2.0 | 1.8 |
| E9 | 66 BA/30 St/4 AA | −18 | 24 | 1.7 | 1.4 |
| E10 | 63.5 BA/31.75 St/4.75 MAA | −12 | 25 | 2.0 | 4.2 |
| C1 | Supra | | 23 | 1.5 | 2.0 |
| Test Series C | | | | | |
| E4 | 60 BA/38 St/2 AA | −10 | 22 | 1.9 | 3.7 |
| E4 | 60 BA/38 St/2 AA | −10 | 19+ | 1.7+ | 2.4+ |
| C1 | Supra | | 22 | 1.8 | 1.5 |
| C1 | Supra | | 10+ | 1.5+ | 2.2+ |
| Test Series D | | | | | |
| E11 | 60 BA/40 MMA | −9 | 15 | 2.1 | 2.2 |
| E12 | 60 BA/38 MMA/2 AA | −9 | 25 | 2.4 | 3.4 |
| C1 | Supra | | 25 | 3.1 | 4.2 |
| Test Series E | | | | | |
| E14 | 60 BA/36 MMA/4 AA | −9 | 21 | 2.1 | 2.2 |
| E6 | 60 BA/37 MMA/3 AA | −9 | 25 | 2.1 | 2.8 |
| E12 | 60 BA/38 MMA/2 AA | −9 | 25 | 1.8 | 2.6 |
| C1 | Supra | | 25 | 2.1 | 3.3 |
| Test Series F | | | | | |
| E20 | 100 EA | −22 | 1 | 1.1 | 1.0 |
| E21 | 70 EA/30 St | 5 | 0 | 1.2 | 4.6 |
| E22 | 70 EA/30 MMA | 6 | 7 | 2.0 | 4.3 |
| Airflex HS-100$^1$ | E/VAc/Acid | — | 0 | 0.8 | 3.8 |

Notes for Table I:
+Fabrics cured at 107° C. for 1.5 minutes
$^1$Trademark Air Products Co.
$^2$Binder E8 copolymer - viscosity average molecular weight is 400,000

EXAMPLE 3-Rayon/Polyester (1/1) Nonwoven Fabrics

Using the same general methods as in Example 2 fabrics are prepared from a web consisting of an equal weight mixture of rayon and polyester fibers. The fibers are DuPont Dacron® Type 54W (1.5 denier-4.0 cm) and FMC Viscose Rayon (1.5 denier-4.0 cm). The finished fabric weighs 23.7 grams per square meter and contains 30% binder on fabric weight. The properties of the fabrics and description of the binders are in Table II which reports the data of a single test series using another crosslinking binder, C2, as a control.

TABLE II

Properties of Rayon/Polyester (1/1) Nonwoven Fabrics (23.7g./m.$^2$ with (30% binder)

| Binder | Composition | Water Wet Abrasion Resistance (Washes Survived) | Water Wet MD Tensile Strength (Kg.) | Hand Panel Test 1.0 = Softest |
|---|---|---|---|---|
| E1 | 58.5 BA/37.5 St/4 AA | 18 | 1.6 | 5.0 |
| C2 | 77 BA/19.5 St/1.5 MOA/2 MAA | 25 | 1.2 | 2.7 |

EXAMPLE 4-Polypropylene Nonwoven Fabrics

Polymer emulsions used in this example are prepared as in Example 1 except for the commercial materials and others used as controls. The latex emulsion is diluted to 4% to 10% solids with water. A wetting agent such as fluorosurfactant may be added but none is necessary; addition of a fuorosurfactant, when used, is noted in the table below. The nonwoven web is saturated in a bath and passed through nip rollers under 30 lbs. (13.6 kgs) pressure at 7.6 yds./min., 7.0 m/min. The webs are dried at 150° F. (65° C.) for five minutes and then cured at 225° F. (107° C.) for 90 seconds. Following test procedures of Example 2, the results obtained are in Table III.

The carded polypropylene webs weigh 0.75 oz./yd.$^2$ (25.4 g/m$^2$) and are prepared from 3.0 denier 1½ in. (4.0 cm) polypropylene staple lightly thermally prebonded. All additive levels are percent on bath solids. Add-on percent is the grams of binder per 100 g. of fiber. Zonyl® FSN is a nonionic fluorosurfactant sold by duPont.

TABLE III

Properties of Polypropylene Nonwoven Fabrics (25.4g/m$^2$)

Series A - Control Binders

| Binder | Additives$^{(c)}$ (s/s) | Add-on (%) | Tensile Strength (Kg.) Dry | Tensile Strength (Kg.) Wet | Washes Survived 43° C. | Washes Survived 60° C. |
|---|---|---|---|---|---|---|
| C1 | 0.5% Zonyl FSN | 33 | 2.2 | 1.3 | 1 | 2 |
| C1 | 0.14% Zonyl FSN | 44 | 3.2 | 2.4 | 6 | 3 |
| C2 | 0.5% Zonyl FSN | 33 | 2.2 | 1.7 | 4 | 1 |
| C2 | 0.14% Zonyl FSN | 45 | 3.4 | 2.5 | 1 | 0 |
| X-Link$^{(a)}$ 2833 | 0.14% Zonyl FSN | 43 | 3.0 | 1.7 | 1 | 1 |
| Hycar$^{(b)}$ 2600X120 | 0.14% Zonyl FSN | 38 | 2.5 | 1.5 | 1 | 0 |
| C3$^{(d)}$ | 0.5% Zonyl FSN | 28 | 1.0 | 0.8 | 2 | 2 |

$^{(a)}$Trademark National Starch
$^{(b)}$Trademark B. F. Goodrich Chemical Company
$^{(c)}$2.5% NH$_4$NO$_3$ is added to each binder.
$^{(d)}$The composition of control binder C3 is 95.9 EA/4.1 MOA Series B - BA/St Ladder (with 0.5% Zonyl FSN)

Tensile

TABLE III-continued
Properties of Polypropylene Nonwoven Fabrics (25.4g/m²)

Series C - Add-on Level Variation (with 0.17% Zonyl FSN) (continued from previous page)

| Binder | Composition | Add-on (%) | Tensile Strength (Kg.) Dry | Tensile Strength (Kg.) Wet | Washes Survived 43° C. | Washes Survived 60° C. |
|---|---|---|---|---|---|---|
| E1 | 58.5 BA/37.5 St/4 AA | 37 | 5.1 | 4.0 | 25 | 4 |
| E19 | 61 BA/35 St/4 AA | 37 | 5.4 | 4.3 | 25 | 8 |
| E8 | 63.5 BA/32.5 St/4 AA | 36 | 5.4 | 3.9 | 25 | 5 |
| E20 | 66 BA/30 St/4 AA | 36 | 5.1 | 4.3 | 25 | 5 |

Series C - Add-on Level Variation (with 0.17% Zonyl FSN)

| Binder | Composition | Add-on (%) | Tensile Strength (Kg.) Dry | Tensile Strength (Kg.) Wet | Washes Survived 43° C. | Washes Survived 60° C. |
|---|---|---|---|---|---|---|
| E1 | 58.5 BA/37.5 St/4 AA | 10 | 1.7 | 1.3 | 1 | 0 |
| E1 | 58.5 BA/37.5 St/4 AA | 23 | 3.3 | 2.4 | 5 | 1 |
| E1 | 58.5 BA/37.5 St/4 AA | 38 | 5.2 | 4.6 | 17 | 1 |
| E1 | 58.5 BA/37.5 St/4 AA | 46 | 7.1 | 4.9 | 25 | 8 |
| E1 | 58.5 BA/37.5 St/4 AA | 57 | 7.3 | 5.9 | 25 | 15 |
| E8 | 63.5 BA/32.5 St/4 AA | 36 | 5.2 | 3.4 | 11 | 1 |
| E8 | 63.5 BA/32.5 St/4 AA | 50 | 6.6 | 5.8 | 25 | 6 |
| E8 | 63.5 BA/32.5 St/4 AA | 63 | 7.8 | 6.7 | 25 | 2 |

Series D - Acid Level and Acid Type

| Binder | Composition | Add-on (%) | Tensile Strength (Kg.) Dry | Tensile Strength (Kg.) Wet | Washes Survived 43° C. | Washes Survived 60° C. |
|---|---|---|---|---|---|---|
| E21 | 66 BA/31 St/3 AA[1] | 29 | 4.3 | 2.7 | 13 | 1 |
| E22 | 66 BA/30.5 St/3.5 AA[1] | 29 | 3.7 | 2.8 | 12 | 1 |
| E24 | 66 BA/31 St/3 AA + 0.35% Na2CO3 | 30[1] | 4.3 | 2.9 | 12 | 1 |
| E21 | 66 BA/31 St/3 AA | 35 | 5.4 | 3.3 | 13 | 1 |
| E20 | 66 BA/30 St/4 AA | 34 | 5.7 | 3.9 | 17 | 2 |
| E25 | 66 BA/28 St/6 AA | 37 | 5.9 | 3.5 | 12 | 1 |
| E26 | 66 BA/26 St/8 AA | 36 | 4.7 | 2.4 | 5 | 1 |

[1] 0.5% Zonyl FSN added.

Series E - Other Composition Types (with 0.5% Zonyl FSN)

| Binder | Composition | Add-on (%) | Tensile Strength (Kg.) Dry | Tensile Strength (Kg.) Wet | Washes Survived 43° C. | Washes Survived 60° C. |
|---|---|---|---|---|---|---|
| E27 | 60 BA/37 MMA/3 AA | 32 | 4.7 | 2.4 | 7 | 1 |
| E1 | 58.5 BA/37.5 St/4 AA | 34 | 4.8 | 3.3 | 19 | 3 |
| E28 | 59 BA/34.8 MMA/2 MHI/2 HEMA/2 AA | 31 | 3.9 | 2.4 | 8 | 1 |

Series F - Zonyl—FSN Level with Binder E1

| % Zonyl FSN (s/s) | Add-on (%) | Tensile Strength (Kg.) Dry | Tensile Strength (Kg.) Wet | Washes Survived 43° C. | Washes Survived 60° C. |
|---|---|---|---|---|---|
| 0 | 38 | 4.7 | 3.8 | 19 | 10 |
| 0.5 | 35 | 5.2 | 4.2 | 19 | 10 |
| 1.0 | 34 | 4.6 | 3.3 | 10 | 8 |
| 2.0 | 33 | 4.1 | 3.0 | 18 | 8 |
| 5.0 | 34 | 3.4 | 2.5 | 4 | 2 |

Notes for Table III
In the data in Series B note that:
1. At 4 weight percent acrylic acid, and within the range of 58.5% to 66% BA and 37.5% to 30% St, a strong, durable nonwoven fabric is obtained.
2. Generally, the hand of these fabrics gets softer as the level of BA increases.
In Series C note that:
1. As the level of binder in the nonwoven fabric increases, strength and durability increases.
2. About 38% add-on is sufficient to attain excellent strength and durability properties.
In Series D note that:
1. Mole for mole, acrylic acid and methacrylic acid yield comparable web properties.
2. Optimum web properties obtain at 4 weight percent acrylic acid, but 3-6% acid yield satisfactory web properties.
In Series E note that substitution of MMA for St reduces wet strength and wash durability; compare E27 and E1.
And in Series F note that:
1. 0.5% Zonyl FSN yield optimum web properties.
2. High levels of Zonyl FSN decrease web strength and durability.

EXAMPLE 5—1.8 Denier Fiber in Polyproylene Fabric.

The polymer emulsion of binder E8 is diluted to 6% solids, adjusted to pH 7 with ammonia, and divided to form two aliquots of 500 grams each. One aliquot is used without further additives in the preparation of fabric 5A. To the other aliquot is added 0.05 grams of defoamer Nopco® DF-160L (Nopco Chemical Company), 0.24 grams of nonylphenyl poly(8.7)ethoxyethanol, and 0.17 grams of a complex phosphate ester, Dianol® RSS (35%) a moderate foaming wetting agent made by Quaker Chemical Corporation, as the binder for fabric 5B. The binder formulations are padded on the polypropylene web described in Example 4 to give an add-on of 39% in fabric 5A and 40% in fabric 5B. The fabrics are prepared and tested as described in Example 4. The results of the testing are in the following Table.

| Fabric | MD Tensile Strength (kg.) Dry | MD Tensile Strength (kg.) Wet | Washes Survived 43° C. | Washes Survived 60° C. |
|---|---|---|---|---|
| 5A | 6.5 | 5.3 | 19 | 2 |
| 5B | 5.8 | 3.7 | 10 | 1 |

These data indicate that formulation with the various additives effects moderate decreases in the wet tensile strength and the wet abrasion resistance of the fabric.

EXAMPLE 6—Lower Denier Polypropylene Fibers

Binders E8 and E1 diluted to 5% solids, and in the case of binder E8 neutralized to a pH of 7, are padded onto polypropylene webs made from 1.8 denier by 1½ inch (4.0 cm) fiber in the form of a 0.5 oz/yd.² (17 g/m²) polyproylene web. Preparation and testing is as given in Example 4. The results are in the following table:

| Binder | Add-on | MD Tensile Strength (kg.) Dry | MD Tensile Strength (kg.) Wet | Washes Survived 43° C. | Washes Survived 60° C. |
|---|---|---|---|---|---|
| E8 | 56 | 2.5 | 1.9 | 21 | 4 |
| E1 | 52 | 3.4 | 2.5 | 25 | 16 |

EXAMPLE 7—Effect of BA/St Ratio in Binder on Polypropylene Fabric

Following the procedures of Example 4, polypropylene fabrics are prepared and tested using binder copolymers made as in Example 1 having a progression of butyl acrylate to styrene ratios. The webs employed are 1.8 denier by 1½ inch (0.4cm) weighing about 0.4 oz./yd.$^2$ (14 g/m$^2$). The results, in the following table, show that the tensile strength of the wet fabric is quite low if there is either insufficient or too much styrene, or, viewed the other way, if there is too much or too little butyl acrylate.

| Binder | Composition | Add-on (%) | MD Tensile Strength kg | Washes Survived 60° C. | Washes Survived 43° C. |
|---|---|---|---|---|---|
| E30 | 96 BA/4 AA | 48 | 0.36 | 0 | 1 |
| E31 | 85 BA/11 St/4 AA | 47 | 0.73 | 0 | 2 |
| E32 | 75 BA/21 St/4 AA | 48 | 1.7 | 0 | 5 |
| E33 | 70 BA/26 St/4 AA | 48 | 1.9 | 1 | 7 |
| E20 | 66 BA/30 St/4 AA | 48 | 2.4 | 2 | 19 |
| E34 | 40 BA/56 St/4 AA | 50 | 0.5 | 1 | 0 |
| E35 | 30 BA/66 St/4 AA | 50 | 0.3 | 0 | 0 |

EXAMPLE 8—The Acrylic Acid Level in the Binder

Using the same polypropylene web and procedures as used in Example 7, a series of binders having progressively increasing amounts of acrylic acid are prepared by the method of Example 1 and tested. The results in the following table show that over the range 0 to 8% acrylic acid only the 0% acrylic acid sample is deficient in wet tensile strength.

| Binder | Composition | Add-on (%) | MD Tensile Kg | Washes Survived 60° C. | Washes Survived 43° C. |
|---|---|---|---|---|---|
| E36 | 66 BA/34 St | 53 | 1.3 | 1 | 23 |
| E-37 | 66 BA/32 St/2AA | 51 | 1.9 | 1 | 6 |
| E-21 | 66 BA/31 St/3AA | 50 | 2.1 | 3 | 17 |
| E-20 | 66 BA/30 St/4 AA | 48 | 2.4 | 2 | 19 |
| E-25 | 66 BA/28 St/6 AA | 53 | 1.6 | 2 | 12 |
| E-26 | 66 BA/26 St/8 AA | 54 | 1.6 | 2 | 11 |

EXAMPLE 9—Polypropylene Webs Bonded with Binders having Various Comonomers

Using the same web and procedures as in Example 7, polypropylene fabrics are prepared employing a variety of binders as listed in the following table. It is seen that the substitution of acrylonitrile for styrene results in a fabric with low wet strength as does a binder employing a high level of ethyl acrylate. The low strength obtained employing a binder having equal amounts of styrene and methyl methacrylate is not reconcilable with the other data on styrene- and methyl methacrylate-containing systems and appears to be a spurious result.

| Binder | Composition | Add-on (%) | Wet MD Tensile Strength kg | Washes Survived 60° C. | Washes Survived 43° C. |
|---|---|---|---|---|---|
| E38 | 63.5 2-EHA/32.5 St/4 AA | 49 | 2.9 | 1 | 7 |
| E39 | 63.5 IBA/32.5 St/4 AA | 53 | 2.1 | 10 | 7 |
| E40 | 63.5 BA/32.5 AN/4 AA | 50 | 1.0 | 0 | 3 |
| E41 | 53.5 BA/32.5 St/10 EA/4 AA | 46 | 2.1 | 0 | 5 |
| E42 | 63.5 BA/16.25 St/16.25 MMA/4 AA | 51 | 1.2 | 0 | 0 |
| E43 | 91 EA/5 St/4 AA | 47 | 0.6 | 0 | 0 |
| E44 | 46.2 EA/30.8 BA/20 MMA/3 AA | 43 | 0.9 | 0 | 2 |
| E8 | 63.5 BA/32.5 St/4 AA | 50 | 1.6 | 2 | 11 |

EXAMPLE 10—Polyester Fabrics With Binder Compositional Variations

Following the procedures of Example 2 polymer emulsions, prepared by the method of Example 1, are used as binders for the polyester web. The fabric thereby produced is tested as described in Example 2. The results are obtained and tested as two test series, A and B, as recorded in Table IV. Inspection of the data on test series A using compositions having 66% butyl acrylate shows that varying the acrylic acid content produces some changes in the tensile strength but going down to 0% acrylic acid produces a fabric with very little wet abrasion resistance. Compositions having comparatively low or no styrene content are seen to be low in wet tensile strength as are compositions very high in styrene content. The results in test series B show that ethylhexyl acrylate may be substituted for the normal butyl acrylate giving a polymer with a particularly soft hand making it an obvious candidate for uses in which softness and high tensile strength are important. Substitution of acrylonitrile for the styrene in the binder produces a fabric with a harsh hand and rather poor wet abrasion resistance. Comparison of the results of binder E41 with those for binder E8 show that substitution of a modest amount of ethyl acrylate for butyl acrylate produces a decrease in the wet tensile strength and the wet abrasion resistance.

TABLE IV

Properties of Polyester Diaper Coverstock Binder Variations

| Binder | Composition | Water Wet Tensile Strength, MD Kg | Wet Abrasion Resistance (Washes Survived) | Hand Panel Test 1 = Softest |
|---|---|---|---|---|
| Test Series A | | | | |
| E36 | 66 BA/34 St | 1.6 | 0 | 1.0 |
| E37 | 66 BA/32 St/2 AA | 2.7 | 6 | 1.3 |
| E20 | 66 BA/30 St/4 AA | 2.0 | 18 | 2.2 |
| E25 | 66 BA/28 St/6 AA | 1.8 | 16 | 2.2 |
| E26 | 66 BA/26 St/8 AA | 1.7 | 8 | 3.2 |
| E30 | 96 BA/4 AA | 0.3 | 5 | 1.0 |
| E31 | 85 BA/11 St/4 AA | 0.8 | 3 | 1.2 |
| E32 | 75 BA/21 St/ | 2.3 | 10 | 1.7 |

TABLE IV-continued
Properties of Polyester Diaper Coverstock Binder Variations

| Binder | Composition | Water Wet Tensile Strength, MD Kg | Wet Abrasion Resistance (Washes Survived) | Hand Panel Test 1 = Softest |
|---|---|---|---|---|
| E33 | 70 BA/26 St/ 4 AA | 2.6 | 10 | 2.3 |
| E8 (1) | 63.5 BA/32.5 St/4 AA | 2.3 | 18 | 2.8 |
| E1 (2) | 58.5 BA/37.5 St/4 AA | 2.3 | 25 | 3.9 |
| E34 | 40 BA/56 St/ 4 AA | 1.1 | 25 | 4.9 |
| E35 | 30 BA/66 S/ 4 AA | 0.6 | 3 | 5.0 |
| C1 | Control | 2.0 | 25 | 3.7 |

(1) Viscosity average molecular weight 950,000
(2) Viscosity average molecular weight 700,000

| | | Test Series B | | |
|---|---|---|---|---|
| E38 | 63.5 EHA/ 32.5 St/ 4 AA | 3.0 | 5 | 1.2 |
| E-39 | 63.5 IBA/32.5 St/4 AA | 2.8 | 25 | 4.4 |
| E40 | 63.5 BA/32.5 AN/4 AA | 2.2 | 2 | 5.0 |
| E43 | 91 EA/5 St/ 4 AA | 2.3 | 0 | 1.1 |
| E42 | 63.5 BA/16.25 St/16.25 MMA/4 AA | 2.0 | 4 | 2.9 |
| E41 | 53.5 BA/10 EA/32.5 St/ 4 AA | 1.9 | 9 | 2.9 |
| E45 | 66 EA/32.7 MMA/1.3 MAA | 1.2 | 4 | 4.5 |
| C1 | — | 2.0 | 25 | 3.7 |

We claim:

1. A nonwoven fabric consisting essentially of fibers and a binder,
    (A) at least 50%, by weight, of the fibers being hydrophobic fibers having a moisture regain less than 2.5% of the fiber weight at 70° F. and 65% RH,
    (B) the binder being free of formaldehyde condensates and comprising a water-insoluble, hydrophobic, emulsion copolymer of ethylenically unsaturated monomers comprising
        (a) 1 to 8%, by weight, of a monoethylenically unsaturated carboxylic acid or a mixture thereof
        (b) 50 to 75%, by weight, of a $C_4$ to $C_8$ alkyl acrylate or a mixture thereof, and
        (c) 20 to 49%, by weight, of one or more hard monomers, and
    (C) the fabric having a water-wet tensile strength, determined on a 2.5 cm wide specimen having a dry weight between 23 and 26 g/m², of at least 1.5 kg.

2. The fabric of claim 1, the hard monomers being one or more of methyl methacrylate, sytrene and α-methyl styrene.

3. The fabric of claim 2, the molecular weight of the copolymer being greater than 100,000, the binder being from about 10% to 100% of the dry fiber by weight, and the acid being acrylic, methacrylic or a mixture thereof.

4. The fabric of claim 3, the copolymer being thermoplastic, having a glass transition temperature below 30° C. and being a copolymer of monomers other than acrylonitrile.

5. The fabric of claim 4, the hydrophobic fibers being polyester fibers, the copolymer having a weight average molecular weight greater than 300,000, the monomers comprising 1 to 5% acid monomers and the wet tensile strength being at least 2.0 kg.

6. The fabric of claim 5, the copolymer being from 20 to 50% of the dry fiber by weight, the fibers being in a carded array and consisting essentially of polyester fibers.

7. The fabric of claim 6 wherein the monomers comprise (a) 2 to 4% by weight of acid monomers and (b) 55 to 70% by weight of butyl acrylate.

8. The fabric of claim 4, the hydrophobic fibers being polyolefin fibers and the monomers comprising (a) 1 to 6% by weight of acid, (b) 55 to 70% by weight of a $C_4$ to $C_8$ alkyl acrylate or a mixture thereof and (c) 25 to 40% by weight of styrene, α-methyl styrene or a mixture thereof.

9. The fabric of claim 8, a major proportion of the fibers being polypropylene fibers, the copolymer having a weight strength being at least 2.0 kg.

10. The fabric of claim 9, the fibers being in a carded array and consisting essentially of polypropylene fibers and the copolymer being from 30% to 60% of the dry fiber by weight.

11. The fabric of claim 10, the monomers comprising (a) 2 to 4% acid monomers, (b) 55 to 70% butyl acrylate and (c) 28 to 40% styrene.

12. The fabric of claim 8 comprising fluorocarbon surfactant up to 2% by weight of the binder.

13. The fabric of claim 7, the surfactant having surface tensions of about 24 and 23 dynes/cm at 0.01% and 0.1, by weight in water, respectively.

14. The fabric of claim 11 comprising a nonionic fluorocarbon surfactant up to 2% by weight of the binder.

15. The fabric of claim 14, the surfactant having surface tensions of about 24 and 23 dynes/cm at 0.01% and 0.1%, by weight in water, respectively.

16. A process of making a nonwoven, wet-strength fabric which comprises associating the hydrophobic fibers and the emulsion copolymer of claim 1 and drying the fibrous product to render it water resistant.

17. A process of making a nonwoven, wet-strength fabric which comprises associating the hydrophobic fibers and the emulsion copolymer of claim 5 and drying the fibrous product to render it water-resistant.

18. A process of making a nonwoven, wet-strength fabric which comprises associating the hydrophobic fibers and the the emulsion copolymer of claim 8 and drying the fibrous product to render it water-resistant.

19. A disposable sanitary product comprising the fabric of claim 1 as a facing layer adapted to be positioned in contact with a wearer or user.

20. A disposable sanitary product comprising the fabric of claim 5 as a facing layer adapted to be positioned in contact with a wearer or user.

21. A disposable sanitary product comprising the fabric of claim 8 as a facing layer adapted to be positioned in contact with a wearer or user.

22. The fabric of claim 1 in the form of diaper coverstock.

23. The fabric of claim 7 in the form of diaper coverstock.

24. The fabric of claim 11 in the form of diaper coverstock.

* * * * *